United States Patent
Jung et al.

(10) Patent No.: US 11,331,598 B2
(45) Date of Patent: May 17, 2022

(54) METHOD OF ISOLATING BOTULINUM TOXIN FROM BOTULINUM TOXIN-CONTAINING SOLUTION

(71) Applicant: MEDYTOX INC., Cheongju-si (KR)

(72) Inventors: Hyun Ho Jung, Seoul (KR); Gi Hyeok Yang, Cheonan-si (KR); Chang Hoon Rhee, Seoul (KR); Hack Woo Kim, Cheongju-si (KR); Gi Hyuck Ryu, Daejeon (KR); Hyung Pyo Hong, Cheongju-si (KR); Jung Hyun Song, Gunsan-si (KR); Joon Chan Kong, Cheongju-si (KR)

(73) Assignee: MEDYTOX INC., Cheongju-si (KR)

( * ) Notice: Subject to any disclaimer, the term of this patent is extended or adjusted under 35 U.S.C. 154(b) by 0 days.

(21) Appl. No.: 16/338,561

(22) PCT Filed: Nov. 29, 2017

(86) PCT No.: PCT/IB2017/057476
§ 371 (c)(1),
(2) Date: Apr. 1, 2019

(87) PCT Pub. No.: WO2018/065972
PCT Pub. Date: Apr. 12, 2018

(65) Prior Publication Data
US 2020/0009473 A1 Jan. 9, 2020

(30) Foreign Application Priority Data
Oct. 4, 2016 (KR) .................. 10-2016-0127540

(51) Int. Cl.
| | |
|---|---|
| *B01D 15/36* | (2006.01) |
| *C07K 1/18* | (2006.01) |
| *C07K 14/33* | (2006.01) |
| *B01J 47/028* | (2017.01) |

(52) U.S. Cl.
CPC ......... *B01D 15/363* (2013.01); *B01D 15/362* (2013.01); *C07K 1/18* (2013.01); *C07K 14/33* (2013.01)

(58) Field of Classification Search
CPC .............. A61K 38/4893; B01D 15/362; B01D 15/363; B01D 15/361; B01J 47/028
See application file for complete search history.

(56) References Cited

U.S. PATENT DOCUMENTS

| | | | |
|---|---|---|---|
| 5,696,077 A | 12/1997 | Johnson et al. | |
| 5,846,929 A | 12/1998 | Johnson et al. | |
| 9,206,409 B2 * | 12/2015 | Ton ................. | C07K 14/33 |
| 2011/0171226 A1 | 7/2011 | Johnson et al. | |
| 2018/0251741 A1 * | 9/2018 | Kim ................. | B01D 61/147 |

FOREIGN PATENT DOCUMENTS

| | | |
|---|---|---|
| EP | 1185291 A2 | 3/2002 |
| JP | 2011074025 A | 4/2011 |
| KR | 20030060150 A | 7/2003 |
| KR | 1020120105417 A | 9/2012 |
| WO | 9605222 A1 | 2/1996 |
| WO | 2011008713 A1 | 1/2011 |
| WO | 2011050072 A1 | 4/2011 |
| WO | 2015016462 A1 | 2/2015 |
| WO | 2017095062 A1 | 6/2017 |

OTHER PUBLICATIONS

POROS Anion Exchange Resins (ThermoFisher Scientific Product Information Sheet; 2018). (Year: 2018).*
POROS Strong Cation Exchange Resins (ThermoFisher Scientific Product Information Sheet; 2018). (Year: 2018).*
Binz et al., "The Complete Sequence of Botulinum Neurotoxin Type A and Comparison with Other Clostridial Neurotoxins," The Journal of Biological Chemistry, 265:9153-9158 (1990), American Society of Biological Chemists Rockefeller Institute for Medical Research; American Society for Biochemistry and Molecular Biology, American Society for Biochemistry and Molecular Biology.
Eisele et al., "Studies on the dissociation of botulinum neurotoxin type A complexes," Toxicon, 47:555-565 (2011), International Society on Toxinology, Elsevier.
Hasegawa et al., "Characterization of Toxin Complex Produced by a Unique Strain of Clostridium botulinum Serotype D 4947," The Protein Journal, 23:371-378 (2004), Kluwer Academic Publishers—Plenum Publisher.
International Search Report dated Feb. 22, 2018 for International Application No. PCT/IB2017/057476, ISA/KR, Korean Intellectual Property Office, Republic of Korea.
Mantecucco et al., "Tetanus and botulism neurotoxins: a new group of zinc proteases," Trends in Biochemical Sciences, 18:324-327 (1993), Elsevier Inc.
Park et al., "Binding of Clostridium botulinum type B toxin to rat brain synaptosome," FEMS Microbiology Letters, 72:243-247 (1990), Federation of European Microbiological Societies.
Poulain et al., "Neurotransmitter release is blocked intracellularly by botulinum neurotoxin, and this requires uptake of both toxin polypeptides by a process mediated by the larger chain," Proceedings of the National Academy of Sciences of the United States of America, 85:4090-4094 (1988).
Schaniz et al., "Properties and Use of Botulinum Toxin and Other Microbial Nerotoxins in Medicine," Microbiological Reviews, 56:80-99 (1992), American Society for Microbiology Journals.
Simpson, "Molecular Pharmacology of Botulinum Toxin and Tetanus Toxin," Annual Review of Pharmacology and Toxicology, 26:427-453 (1986).
Singh et al., "Critical Aspects of Bacterial Protein Toxins," Advances in Experimental Medicine and Biology, pp. 63-84 (1996), Plenum Press, New York.

(Continued)

*Primary Examiner* — Ryan B Huang
(74) *Attorney, Agent, or Firm* — Potomac Law Group, PLLC

(57) ABSTRACT

Provided is a method of isolating a botulinum toxin type A macro complex from a botulinum toxin-containing solution, the method including performing anion exchange chromatography and cation exchange chromatography.

9 Claims, 1 Drawing Sheet

(56) References Cited

OTHER PUBLICATIONS

Sugiyama, "Clostridium botulinum Neurotoxin," Microbiological Reviews, 44:419-448 (1980), American Society for Microbiology (ASM).

Dasgupta et al., "Cation-exchange chromatography of Clostridium botulinum type a toxin on amberlite IRC-50 resin at pH 5.55", Biochimica Et Biophysica Acta—Protein Structure, 1968, vol. 168(3), pp. 522-531, Elsevier Science BV, Amsterdam, NL.

Dasgupta et al., "Purification of Clostridium botulinum type a toxin", Biochimica Et Biophysica ACTA—Protein Structure, 1970, vol. 214(2), pp. 343-349, Elsevier Science BV, Amsterdam, NL.

Extended European Search Report dated May 4, 2020, issued in European Application No. 17857967.8.

Simpson et al., "Isolation and Characterization of the Botulinum Neurotoxins", Methods in Enzymology, 1988, vol. 165, pp. 76-85, Elsevier, Academic Press, US.

Korean Office Action (Notification of Reason of Refusal) dated Feb. 23, 2022, issued in Korean Application No. 10-2016-0127540, with English translation.

* cited by examiner

[Fig. 1]

```
         WCB
          ▽
          │
          ○── SEED CULTURE
          │
          ○── MAIN CULTURE
          │
          ○── SUPERNATANT RECOVERY
          │
          ○── ACID PRECIPITATION
          │
          ○── AGGREGATE RECOVERY
          │
          ○── SOLUBLE PROTEIN RECOVERY
          │
          ○── CONCENTRATION AND DIAFILTRATION
          │
          ○── ANION EXCHANGE CHROMATOGRAPHY
          │
          ○── CONCENTRATION AND DIAFILTRATION
          │
          ○── CATION EXCHANGE CHROMATOGRAPHY
          │
          ○── CONCENTRATION AND DIAFILTRATION
          │
          ○── FILTRATION
          ▽
PURIFIED BOTULINUM TOXIN
```

[Fig. 2]

Chromatogram showing peaks: HMW2 – 8.592, 19S – 9.456, 12S – 12.308; x-axis TIME (MIN) from 0.00 to 20.00, y-axis AU from 0.00 to 1.30.

METHOD OF ISOLATING BOTULINUM TOXIN FROM BOTULINUM TOXIN-CONTAINING SOLUTION

CROSS-REFERENCE TO RELATED APPLICATION

This application claims the benefit of Korean Patent Application No. 10-2016-0127540, filed on Oct. 4, 2016, in the Korean Intellectual Property Office, the disclosure of which is incorporated herein in its entirety by reference.

TECHNICAL FIELD

The present disclosure relates to a method of isolating botulinum toxin from a botulinum toxin-containing solution.

BACKGROUND ART

*Clostridium* strains which secrete toxins having neurotoxicity have been discovered from 1890 until the present day, and research into the properties of toxins secreted by these strains has been conducted for the past 70 years (Schant, E. J. et al., Microbiol. Rev. 56; 80; 1992).

The genus *Clostridium* includes more than 127 species, which are divided according to their morphology and functions. *Clostridium botulinum* is an anaerobic and Gram-positive bacterium which produces a strong polypeptide neurotoxin that causes a neuroparalytic illness, known as botulism, in humans and animals. Spores of *Clostridium botulinum* are found in soil, and a large amount of these spores may even cultured even be cultured in foods which have not been processed properly. These spores may cause many forms of botulism.

Botulinum toxin is divided into seven types of A through G according to their serological characteristics. Each toxin includes about 150 kDa of toxin protein, and naturally is composed of a complex with a variety of non-toxic proteins bound thereto. An intermediate complex (300 kDa) is composed of a toxin protein and a non-toxic non-hemaglutinin (HA) protein, and a large complex (500 kDa) and a macro complex (900 kDa), each have a structure in which the intermediate complex is bound to hemaglutinin (Sugiyama, H., Microbiol. Rev., 44, 419; 1980). Such non-toxic non-hemaglutinin proteins are known to protect the toxin from low pH and various kinds of protein hydrolytic enzymes in intestines (Sugiyama, H., Microbiol. Rev., 44, 419; 1980).

Botulinum toxin is synthesized in a cell as a single-chain polypeptide with a molecular weight of approximately 150 kDa, and then cleaved into two subunits of a light chain (a molecular weight of 50 kDa) and a heavy chain (a molecular weight of 100 kDa) at a position that is one-third the distance from the N-terminus by action of intracellular protease or by artificial treatment with an enzyme such as trypsin. Such a cleaved toxin has highly increased toxicity in comparison with the single-chain polypeptide. The two subunits are bound to each other by a disulfide bond, and each subunit has a different function. The heavy chain binds with a receptor of a target cell (FEMS Microbiol. Lett. 72, 243; 1990), and reacts with a bio-membrane at a low pH (pH 4.0) to form a channel (Mantecucco, C. et al., TIBS 18, 324; 1993), and the light chain has pharmacological activities, and thus interferes with secretion of neuro-transmitters, when cells are provided with permeability by a surfactant or the light chain is introduced into cells by electroporation, (Poulain, B. et al., Proc. Natl. Acad. Sci. USA. 85, 4090; 1988).

Botulinum toxin type A is a natural biological agent which is known to be the most lethal to humans. On a molar basis, botulinum toxin type A is 1.8 billion times more lethal than diphtheria toxin, 600 million times more lethal than sodium cyanide, 30 million times more lethal than cobratoxin, and 12 million times more lethal than cholera toxin (Singh, Critical Aspects of Bacterial protein Toxins, page 63-84 of natural toxins II, edited by B. R. Sigh et al., Plenum Press, New York (1976)).

Botulinum toxin inhibits exocytosis of acetylcholine at a cholinergic presynapse of a neuromuscular junction, thereby causing asthenia. Taking into account that toxicity is exhibited even with exposure to a very small amount of botulinum toxin, it has been considered that this toxin may have enzymatic activity (Simpson, L. L. et al., Ann. Rev. Pharmaeol. Toxicol. 26, 427; 1986). According to recent reports, botulinum toxin has metallopeptidase activity, and substrates thereof are unit proteins of an exocytosis machinery complex, such as synaptobrevin, syntaxin, synaptosomal associated protein of 25 kDa (SNAP 25), etc. Each type of botulinum toxin uses one of the three proteins as a substrate, and it is known that botulinum toxin types B, D, F, and G cleave synaptobrevin at a specific site, botulinum toxin types A and E cleave SNAP25 at a specific site, and botulinum toxin type C cleaves syntaxin at a specific site (Binz, T. et al., J. Biol. Chem. 265, 9153; 1994).

Korean Patent Publication NO. 10-2012-0105417 discloses a method of isolating botulinum toxin from a culture of *Clostridium botulinum*, the method including recovering the biologically active *botulinum* neurotoxin from a fermentation medium by contacting the fermentation medium with an anion exchange chromatography medium and then contacting an eluent from the anion exchange chromatography medium with a cation exchange chromatography medium. In this method, elution is performed after binding the toxin to the anion exchange chromatography medium, but the method does not disclose flowing of the toxin without binding it to the medium.

According to the method, there is a problem in that during purification of the botulinum toxin protein, a neurotoxic component (i.e., a neurotoxic molecule of approximately 150 kDa), an intermediate complex (300 kDa), or a large complex (500 kDa) is dissociated and removed from the botulinum toxin protein.

DISCLOSURE OF INVENTION

Technical Problem

An aspect provides a method of isolating a botulinum toxin type A macro complex from a botulinum toxin-containing solution.

Solution to Problem

An aspect provides a method of isolating a botulinum toxin type A macro complex from a botulinum toxin-containing solution, the method including contacting the botulinum toxin-containing solution with an anion exchange chromatography medium at a pH lower than an isoelectric point (PI) of botulinum toxin; contacting the solution, which is not bound to the anion exchange chromatography medium, with a cation exchange chromatography medium at a pH lower than PI of botulinum toxin; and separating the botulinum toxin type A macro complex from the cation exchange chromatography medium; or contacting the botulinum toxin-containing solution with the cation exchange chromatography medium at a pH lower than PI of botulinum toxin; separating *botulinum* toxin from the cation exchange chromatography medium; contacting the solution containing the toxin separated from the cation exchange chromatography medium, with the anion exchange chromatography medium at a pH lower than PI of *botulinum* toxin; and separating the botulinum toxin type A macro complex from the solution which is not bound to the anion exchange chromatography medium.

The method includes contacting the botulinum toxin-containing solution with the anion exchange chromatography medium at a pH lower than an isoelectric point (PI) of botulinum toxin; contacting the solution, which is not bound to the anion exchange chromatography medium, with the cation exchange chromatography medium at a pH lower than PI of botulinum toxin; and separating the botulinum toxin type A macro complex from the cation exchange chromatography medium.

As used herein, the "botulinum toxin type A macro complex" may be a dimer of two 16S toxins linked via HA1 which is one of HA proteins, each 16S toxin, i.e., a toxin of about 500 kDa, is composed of botulinum toxin (BoNT), non-toxic non-HA (NTNHA), and HA components.

The method includes contacting the botulinum toxin-containing solution with the anion exchange chromatography medium at a pH lower than PI of botulinum toxin.

In the above process, the botulinum toxin-containing solution may be a culture of *Clostridium botulinum* or a solution derived therefrom. The solution derived therefrom may be a solution obtained by partially purifying the toxin from the culture. Culturing of *Clostridium botulinum* may be performed by a known method. The culturing may be performed in a medium containing plant-derived components. The culturing is performed by using the medium containing plant-derived components, thereby expressing the toxin outside cells, unlike the prior art. As used herein, the "expressing the toxin outside cells" indicates that, after the cells produce the toxin therein, the cells excrete the toxin spontaneously, and the cells containing the toxin expressed therein are also lysed, whereby the toxin is exposed to a solution of the culture, not inside the cells of the culture.

The medium containing plant-derived components may include phytone peptone, and preferably, phytone peptone, yeast extract, and glucose. In addition, the medium containing plant-derived components may further include one or more components selected from the group consisting of vegetable tryptone, soytone, and sodium thioglycolate. Further, the medium containing plant-derived components may be a medium selected from the group consisting of a medium containing glucose, yeast extract, and phytone peptone; a medium containing glucose, yeast extract, phytone peptone, and vegetable tryptone; a medium containing glucose, yeast extract, phytone peptone, and soytone; a medium containing glucose, yeast extract, soytone, and vegetable tryptone; a medium containing glucose, yeast extract, sodium thioglycolate, phytone peptone, vegetable tryptone, and soytone; and a medium containing glucose, yeast extract, phytone peptone, vegetable tryptone, and soytone.

Further, amounts of glucose, yeast extract, sodium thioglycolate, phytone peptone, vegetable tryptone, and soytone in each medium described as the medium containing plant-derived components may be 0.2% to 2%, 0.5% to 5%, 0.05% to 2%, 0.5% to 2%, 0.5% to 2%, and 0.5% to 2%, respectively, based on a total weight of the medium. The medium containing plant-derived components may be selected from the group consisting of a medium containing glucose, yeast extract, and phytone peptone; a medium containing glucose and yeast extract; a medium containing glucose, yeast extract, phytone peptone, and vegetable tryptone; a medium containing glucose, yeast extract, phytone peptone, and soytone; a medium containing glucose, yeast extract, soytone, and vegetable tryptone; a medium containing glucose, yeast extract, sodium thioglycolate, phytone peptone, vegetable tryptone, and soytone; and a medium containing glucose, yeast extract, phytone peptone, vegetable tryptone, and soytone. Amounts of glucose, yeast extract, sodium thioglycolate, phytone peptone, vegetable tryptone, and soytone in each medium described above are 0.2% to 2%, 0.5% to 5%, 0.05% to 2%, 0.5% to 2%, 0.5% to 2.0%, and 0.5% to 2%, respectively, based on a total weight of the medium, and the rest of the medium may be composed of water.

The toxin may be selected from the group consisting of botulinum toxin A, B, C, D, E, F and G, and preferably, the toxin may be type A toxin. An isoelectric point of botulinum toxin A may be about 6.06. Therefore, the "pH lower than the isoelectric point" may differ depending on the type of the toxin to be isolated. For example, in the case of type A toxin, the pH may be 6.06 or lower, 6.05 or lower, 6.00 or lower, 5.7 or lower, 5.5 or lower, 5.0 or lower, 4.5 or lower, 4.0 or lower, or 3.5 or lower. In the case of type A toxin, the pH may be 2.5 to 6.05, 3.0 to 6.00, 3.5 to 5.5, 3.5 to 5.0, 3.5 to 4.5, 3.5 to 4.0, 3.5 to 6.00, 4.0 to 6.0, 4.5 to 6.0, 5.5 to 6.0, 4.0 to 5.5, or 4.5 to 5.5.

An anion exchange resin used in the anion exchange chromatography may be a resin substituted with a diethylaminoethyl (DEAE) group or a quaternary ammonium (Q) group, but is not limited thereto. For example, DEAE-Sephadex as described in U.S. Pat. No. 5,696,077, International Patent Publication NO. WO96/05222, and U.S. Pat. No. 5,846,929 may be used. Preferably, any one selected from anion exchange resins having a strong basic quaternary ammonium group or a weak basic diethylaminoethyl (DEAE) group may be used.

For example, the strong basic anion exchange group may be Q Sepharose Fast Flow, Q Sepharose High Performance, Resource Q, Source 15Q, Source 30Q, Mono Q, Mini Q, Capto Q, Capto Q ImpRes, Q HyperCel, Q Cermic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-6505, TSKgel SuperQ-5PW (30), TSKgel SuperQ-5PW (20), TSKgel SuperQ-5PW, etc., but is not limited thereto. Any anion exchange resin known in the art may be used.

By the anion exchange chromatography, *Clostridium botulinum* toxin may flow out without binding to the medium, and impurities bind to the medium. The liquid flowing out of the chromatography may be used in further separation.

In the above process, the contacting may include flowing of the botulinum toxin-containing solution into the medium, for example, flowing of the botulinum toxin-containing solution into the medium packed in a column under predetermined conditions. Conditions such as a flow rate, temperature, time, etc. may be controlled. In the contacting, a phosphate buffer solution, a citrate buffer solution, or an acetate buffer solution may be used as a column buffer solution. A concentration of the column buffer solution may be controlled from 5 mM to 30 mM, for example, from 7 mM to 27 mM, from 10 mM to 25 mM, or from 15 mM to 20 mM. A flow rate of a mobile phase may be 0.5 ml/min to 5.0 ml/min, 1.0 ml/min to 30.0 ml/min, 10 ml/min to 30.0 ml/min, or 15 ml/min to 25.0 ml/min. In this regard, after conductivity of the buffer solution may be adjusted at 3 mS/cm to 30 mS/cm and column equilibration is finished, a sample may be injected.

Further, the method may include contacting the solution, which is not bound to the medium, with the cation exchange chromatography medium at a pH lower than PI of botulinum toxin. The "pH lower than PI" and "contacting" are the same as described above.

In the above process, the cation exchange chromatography medium may be a medium having a strong acidic cation exchange group such as sulfopropyl (SP) and methyl sulfonate (S) or a weak acidic cation exchange group such as carboxymethyl (CM).

Further, the method includes separating the botulinum toxin from the cation exchange chromatography medium. Separating of the toxin may include recovering of the botulinum toxin from an elution solvent by contacting the medium with the elution solvent. Any elution solvent may be used, as long as it may separate the toxin from the medium. The elution solvent may be, for example, a buffer solution used in the buffering of the column or the buffer solution of which a salt concentration or conductivity may be properly controlled. The salt may be a salt of Na or K. The column buffer solution may be a phosphate buffer solution, a citrate buffer solution, or an acetate buffer solution. A concentration of the column buffer solution may be controlled from 5 mM to 100 mM, for example, from 10 mM to 100 mM, from 20 mM to 100 mM, or from 30 mM to 70 mM. A flow rate of the elution solvent which is a mobile phase may be 0.5 ml/min to 5.0 ml/min, 1.0 ml/min to 150.0 ml/min, 50.0 ml/min to 150.0 ml/min, or 75.0 ml/min to 125.0 ml/min. In this regard, conductivity of the elution solvent may be 3 mS/cm to 30 mS/cm. The elution solvent may be a phosphate buffer (50 mM, pH 5.0) containing 0.5 M to 2.0 M NaCl, for example, 1.0 M NaCl.

The method may further include adjusting the pH of the botulinum toxin or the botulinum toxin-containing solution to a pH lower than PI of botulinum toxin, before contacting with the anion exchange chromatography medium, before contacting with the cation exchange chromatography medium, or before each of these two processes. The adjusting may include mixing the botulinum toxin or the botulinum toxin-containing solution with a buffer having a pH lower than PI of botulinum toxin. The buffer may be a phosphate buffer, a citrate buffer, an acetate buffer, or a mixture thereof. The buffer may have pH of 3.5 to 6.5, or pH of 3.5 to 5.5. The buffer may include 10 mM to 100 mM phosphate, citrate, or acetate.

The method may further include performing ultrafiltration of the botulinum toxin-containing solution, before contacting with the anion exchange chromatography medium, before contacting with the cation exchange chromatography medium, or before each of these two processes. The ultrafiltration may be performed by using a membrane with a molecular weight cut-off of 25 kDa to 125 kDa. The ultrafiltration may be adjusted such that a molecular weight cut-off before contacting with the cation exchange chromatography medium, for example, a molecular weight cut-off of 50 kDa may be lower than a molecular weight cut-off before contacting with the anion exchange chromatography medium, for example, a molecular weight cut-off of 100 kDa.

The method includes expressing *Clostridium botulinum* toxin outside cells by culturing *Clostridium botulinum* in a medium, before contacting with the anion exchange chromatography medium, and the botulinum toxin-containing solution may be a portion containing *Clostridium botulinum* toxin expressed outside cells by removing the cells from the obtained culture.

The method includes expressing *Clostridium botulinum* toxin outside cells by culturing *Clostridium botulinum* in a medium, before contacting with the anion exchange chromatography medium; and precipitating the toxin by adding an acid to a culture solution which is obtained by removing the cells from the culture, and then separating precipitates; and dissolving the precipitates in a medium and performing ultrafiltration, wherein the botulinum toxin-containing solution may be a solution obtained by the ultrafiltration.

In the method, removing of the cells may be performed by one or more filtrations selected from the group consisting of depth filtration and microfiltration, precipitation of the toxin may be performed by maintaining the culture at pH 3 to pH 4 with an acid, and ultrafiltration may be performed by using a membrane with a molecular weight cut-off of 100 kDa or less.

Another aspect provides a method of isolating botulinum toxin from the *botulinum* toxin-containing solution, the method including contacting the botulinum toxin-containing solution with the cation exchange chromatography medium at a pH lower than PI, separating the botulinum toxin from the cation exchange chromatography medium, contacting the solution containing the toxin which is separated from the medium, with the anion exchange chromatography medium at a pH lower than PI, and isolating the botulinum toxin from the solution which is not bound to the medium.

The contacting of the botulinum toxin-containing solution with the cation exchange chromatography medium at a pH lower than PI and the separating of the *botulinum* toxin from the cation exchange chromatography medium are the same as described above, except that the botulinum toxin-containing solution is used instead of "the solution which is not bound to the medium". Further, "the contacting of the solution containing the toxin which is separated from the medium, with the anion exchange chromatography medium at a pH lower than PI, and the isolating of the *botulinum* toxin from the solution which is not bound to the medium" are the same as described above, except that "the solution containing toxin which is separated from the medium" is used instead of "the botulinum toxin-containing solution".

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Advantageous Effects of Invention

According to the method of isolating botulinum toxin from the botulinum toxin-containing solution of an aspect, botulinum toxin type A macro complex, i.e., 900 kDa may be efficiently isolated from the botulinum toxin-containing solution.

BRIEF DESCRIPTION OF DRAWINGS

These and/or other aspects will become apparent and more readily appreciated from the following description of the embodiments, taken in conjunction with the accompanying drawings in which:

FIG. 1 is a schematic view showing a process of purifying *Clostridium botulinum* type A toxin from a culture of *Clostridium botulinum*; and FIG. 2 is a schematic view showing results of SEC-HPLC of a sample obtained by cation exchange chromatography.

BEST MODE FOR CARRYING OUT THE INVENTION

Hereinafter, the present invention will be described in more detail with reference to Examples. However, these Examples are for illustrative purposes only, and the scope of the invention is not intended to be limited by these Examples.

Example 1

Culture of *Clostridium botulinum* and Purification of *Clostridium botulinum* Toxin 1. Culture of *Clostridium botulinum*

In this Example, a large amount of *Clostridium botulinum* type A toxin was expressed outside cells by culturing *Clostridium botulinum* in an animal product-free medium.

The used medium was a medium containing 4% yeast extract and 0.5% glucose, based on a total weight of the medium. The components of the medium were dissolved in water for injection (WFI), and pH was adjusted with NaOH to 7.2.

200 ml of the medium thus prepared was filtered through a sterile single use microfiltration system (0.2 µm Sartorius 2, manufactured by Sartorius), and injected into Cellbag™ (manufactured by GE healthcare, a single use fermentation bag). Then, the medium was inoculated with 1 ml of a seed culture of *Clostridium botulinum* at a density of $10^6$ cells/ml~$10^7$ cells/ml through a sample injection port. Cellbag™ is a disposable bioreactor that uses rocking motion in order to cause mixing under low shear stress. Cellbag™ is a bag including an air inlet and outlet and a sample port, and is composed of a flexible material, and the bag is air impermeable. In addition, the bag is equipped with a pump combined thereto, which is used for bag inflation and cell supply. The used bag has a volume of 2 L.

Culturing was performed such that 2 L Cellbag™ containing 200 ml of the species culture was species-cultured at 37° C. for 12 hours to 30 hours under rocking at 10 rpm by using a rocker unit in Cellbag™, and the resultant was inoculated in a bag containing 20 L of a main culture medium through a sterile single use connector (Kleenpack connector PALL) made of polycarbonate, and then cultured for 48 hours to 72 hours while maintaining anaerobic conditions. A sterile filter (0.2 µm) was installed at the sample injection port of the bag, and 200 ml of the species culture medium was injected into the bag through the sterile filter. The injection of the medium was performed using a peristaltic pump.

The species culture medium was injected to the bag without a headspace so as to maintain anaerobic conditions. The species culture was also injected in the same manner. In addition, the main culture was performed by mounting the bag on a platform of the rocker unit of Cellbag™ and rocking the bag at 10 rpm at a temperature of 37° C. During the main culture, 1800 L of nitrogen was purged for 6 hours in order to maintain anaerobic conditions inside the bag, and the culture temperature may be 34° C., 35° C., or 36° C., in addition to 37° C.

After the culturing was terminated, a QDC connector (manufactured by Satorious) which is a sterile connector was connected to the sample port of the bag, and the culture was transferred to another disposable bag (flexible disposable bag) through the sterile connector. Then, a sterile disposable depthfilter (Sartoclear or SupraCap, PALL) and microfilter (0.2 µm, Sartopore 2, Sartorius) were connected to the disposable container containing the culture, and the culture was filtered therethrough to remove the cells. Then, the obtained supernatant was put in another disposable bag. From the supernatant, *Clostridium botulinum* toxin was purified.

2. Purification of *Clostridium botulinum* Toxin from Culture

Hereinbelow, a method of producing type A toxin from the cell-removed culture will be described in detail.

(1) Acid Precipitation

1 N sulfuric acid was added to a bag containing 20 L of the culture supernatant obtained as above to adjust pH from 3.0 to 4.5, and as a result, toxin protein was precipitated. All procedures of this process were also performed in a disposable sample bag without being in contact with the outside.

Then, when the precipitation was completed, the resulting solution was filtered through a sterile disposable filtration system (disposable slice 200 0.2 µm filter, manufactured by Sartorius) without being in contact with the outside, thereby removing the supernatant, and the precipitate was collected in a disposable sample bag. 5 L of WFI was added to the collected precipitate to wash sulfuric acid, and a sterile disposable microfiltration system (disposable slice 200 0.2 µm filter) was connected to the bag and the supernatant was removed. As a result, the precipitate was collected into a disposable bag.

(2) Concentration and Filtration

10 L of citrate buffer (25 mM, pH 5.5) was added to the collected precipitate to redissolve toxin protein existing in the precipitate. This process was also performed in a disposable bag without being in contact with the outside. A sterile disposable filtration system (0.2 µm, ULTA Cap HC, GE, USA) was connected to the bag containing the re-dissolved sample, and filtration was performed without being in contact with the outside. As a result, the supernatant was collected in a sterile disposable bag and insoluble impurities were removed.

A sterile disposable ultrafiltration membrane (disposable slice 200 100 kDa, manufactured by Sartorius) having a molecular weight cut-off of 100 kDa was connected to the bag containing the sample from which the insoluble impurities were removed. Then, the sample was filtered without being in contact with the outside to be concentrated. Even in this process, toxin protein was in contact with an inner surface of the sterile container, and not in contact with the outside.

(3) Anion Exchange Chromatography

Next, a disposable DEAE anion exchange chromatography system (DEAE BPG Column™: GE Healthcare) was connected to the bag containing the sample after the concentration and buffer exchange were completed, and DEAE anion exchange chromatography was performed without being in contact with the outside. In detail, the citrate buffer (25 mM pH 5.5) was passed through a column packed with a DEAE anion exchange resin to equilibrate the column, and the toxin-containing citrate buffer (25 mM pH 5.5) was passed through the column. In this process, *Clostridium botulinum* type A toxin was not adsorbed to the anion exchange resin, and most impurities were adsorbed thereto and removed. A flow rate was 20 ml/min, and pH was maintained at 5.5.

(4) Concentration and Filtration

Next, a fraction containing *Clostridium botulinum* type A toxin was collected from the flow-through solutions which were not bound to the anion exchange resin during the anion exchange chromatography.

A sterile disposable ultrafiltration membrane (disposable slice 200 100 kDa, manufactured by Sartorius) having a molecular weight cut-off of 50 kDa was connected to the bag containing the fraction, and concentration was performed by filtration without being in contact with outside, and buffer exchange was performed by using a phosphate buffer (50 mM pH 5.0). Even in this process, toxin protein was in contact with an inner surface of the sterile container, and not in contact with the outside. As the buffer used in the buffer exchange, 10 mM to 75 mM phosphate buffer, citrate buffer, or acetate buffer having pH of 3.5 to 6.5, or pH of 3.5 to 5.5 lower than pI of *Clostridium botulinum* toxin may be also used, in addition to the phosphate buffer (50 mM pH 5.0).

(5) Cation Exchange Chromatography

Next, a disposable SP cation exchange chromatography system (GE healthcare, SP sepharose FF) was connected to the bag containing the sample obtained by buffer exchange, and cation exchange chromatography was performed without being in contact with outside. In detail, the phosphate buffer (75 mM pH 5.0) was passed through a column packed with a SP cation exchange resin to equilibrate the column, and the sample was passed through the column. In this process, *Clostridium botulinum* type A toxin was adsorbed to the cation exchange resin. This procedure was performed for 25 minutes at a flow rate of 100 ml/min, and pH was maintained at 5.0. Then, elution was performed by using a phosphate buffer (75 mM pH 5.0) containing 1 M NaCl.

The obtained sample was subjected to size exclusion chromatography (SEC-HPLC) and purity of the toxin was analyzed. As a mobile phase, a 40 mM phosphate solution of pH 6.5 was used. SRT SEC-500 (manufactured by Sepax Technologies, P/N 215500) column was connected, and 40 µL of *botulinum* type A toxin protein was loaded and passed through the column for 20 minutes at 0.8 mL/min.

FIG. 1 is a schematic view showing the process of purifying *Clostridium botulinum* type A toxin from the culture of *Clostridium botulinum*.

FIG. 2 is a schematic view showing results of SEC-HPLC of the sample obtained by cation exchange chromatography.

TABLE 1

| Name | Retention time (min) | Area | % Area |
| --- | --- | --- | --- |
| 12S | 12.306 | 77163 | 0.19 |
| 19S | 9.459 | 40065228 | 99.64 |
| HMW1 | 7.000 | — | — |
| HMW2 | 8.578 | 127860 | 0.32 |

Table 1 shows data of peaks of FIG. 2, and purity of type A toxin was 99.64%. In particular, HMW1 appearing at a retention time (RT) was 0%, indicating absence. In Table 1, HMW1 and HMW2 represent aggregate 1 and aggregate 2, respectively and 12S (300 kDa) and 19S (900 kDa) are regarded as 12S toxin (also called "M toxin" consisting of BoNT toxin and non-toxic non-HA (NTNHA) and a dimer of two 16S toxins linked via HA1 which is one of HA proteins, each 16S (500 kDa) toxin consisting of BoNT, NTNHA, and HA components. The HA component has three different proteins, i.e., HA1, HA2 and HA3. Toxin type A has forms of 12S, 16S, and 19S.

Therefore, according to the purification method, a macro complex of botulinum toxin type A which is not dissociated may be isolated with high purity.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

INDUSTRIAL APPLICABILITY

Therefore, according to the purification method, a macro complex of botulinum toxin type A which is not dissociated may be isolated with high purity.

The invention claimed is:

1. A method of isolating a botulinum toxin type A macro complex from a botulinum toxin-containing solution, the method comprising:
    culturing *Clostridium botulinum* in an animal product-free medium to obtain a culture;
    removing *Clostridium botulinum* cells from the culture to obtain a botulinum toxin-containing solution;
    adding an acid to the botulinum toxin-containing solution to precipitate the botulinum toxin and obtain a precipitate;
    dissolving the precipitate in a medium to obtain a solution;
    filtering the solution to obtain a botulinum toxin-containing solution; and
    (a) contacting the botulinum toxin-containing solution with an anion exchange chromatography medium at a pH lower than an isoelectric point (PI) of botulinum toxin;
    contacting a flow-through portion of the botulinum toxin-containing solution, which is not bound to the anion exchange chromatography medium, with a cation exchange chromatography medium at a pH lower than the PI of botulinum toxin; and
    separating the botulinum toxin type A macro complex from the cation exchange chromatography medium; or
    (b) contacting the botulinum toxin-containing solution with a cation exchange chromatography medium at a pH lower than a PI of botulinum toxin;
    separating botulinum toxin from the cation exchange chromatography medium;
    contacting a solution containing the botulinum toxin separated from the cation exchange chromatography medium with an anion exchange chromatography medium at a pH lower than the PI of botulinum toxin; and
    separating the botulinum toxin type A macro complex from a flow-through portion of the solution containing the botulinum toxin, which is not bound to the anion exchange chromatography medium.

2. The method of claim 1, further comprising
    adjusting a pH of the botulinum toxin-containing solution to a pH lower than the PI of botulinum toxin, before the contacting of the botulinum toxin-containing solution with the anion exchange chromatography medium at the pH lower than the PI of botulinum toxin in (a);

adjusting a pH of the flow-through portion of the botulinum toxin-containing solution that is not bound to the anion exchange chromatography medium, before the contacting of the flow-through portion of the botulinum toxin-containing solution with the cation exchange chromatography medium at the pH lower than the PI of botulinum toxin in (a);

adjusting a pH of the botulinum toxin-containing solution, before the contacting of the botulinum toxin-containing solution with the cation exchange chromatography medium at the pH lower than the PI of botulinum toxin in (b); or adjusting a pH of the solution containing the botulinum toxin separated from the cation exchange chromatography medium, before the contacting of the solution containing the botulinum toxin separated from the cation exchange chromatography medium with the anion exchange chromatography medium at the pH lower than the PI of botulinum toxin in (b).

3. The method of claim 2, wherein the adjusting comprises mixing the botulinum toxin-containing solution, the flow-through portion of the botulinum toxin-containing solution, or the solution containing the botulinum toxin with a buffer having a pH lower than the PI of botulinum toxin.

4. The method of claim 3, wherein the buffer is a phosphate buffer, a citrate buffer, or an acetate buffer.

5. The method of claim 3, wherein the buffer has a pH of 3.5 to 6.0.

6. The method of claim 3, wherein the buffer comprises a 10 mM to 100 mM phosphate buffer, a 10 mM to 100 mM citrate buffer, or a 10 mM to 100 mM acetate buffer.

7. The method of claim 1, wherein the anion exchange chromatography medium comprises DEAE or Q anion exchange resin.

8. The method of claim 1, wherein the cation exchange chromatography medium comprises CM, S, or SP cation exchange resin.

9. The method of claim 1, wherein the pH lower than the PI of botulinum toxin is pH 3.5 to 6.0.

* * * * *